(12) United States Patent
Farnsworth et al.

(10) Patent No.: US 9,027,560 B2
(45) Date of Patent: May 12, 2015

(54) BREATHING GAS DELIVERY SYSTEM AND METHOD

(75) Inventors: Albert W. Farnsworth, Hemet, CA (US); Wolff M. Kirsch, Redlands, CA (US); Yong Hua Zhu, Redlands, CA (US)

(73) Assignees: Loma Linda University, Loma Linda, CA (US); Faculty Physicians and Surgeons of LLUSM, Loma Linda, CA (US)

( * ) Notice: Subject to any disclaimer, the term of this patent is extended or adjusted under 35 U.S.C. 154(b) by 1838 days.

(21) Appl. No.: 11/775,841

(22) Filed: Jul. 10, 2007

(65) Prior Publication Data

US 2008/0142012 A1 Jun. 19, 2008

Related U.S. Application Data

(60) Provisional application No. 60/819,751, filed on Jul. 10, 2006, provisional application No. 60/844,125, filed on Sep. 11, 2006.

(51) Int. Cl.
| | |
|---|---|
| *A61M 15/08* | (2006.01) |
| *A62B 18/10* | (2006.01) |
| *A61M 16/06* | (2006.01) |
| *A61M 16/00* | (2006.01) |
| *A61M 16/20* | (2006.01) |

(52) U.S. Cl.
CPC .......... *A61M 16/0666* (2013.01); *A61M 16/00* (2013.01); *A61M 16/20* (2013.01); *A61M 16/208* (2013.01); *A61M 2016/0015* (2013.01); *A61M 2202/0208* (2013.01); *A61M 2230/42* (2013.01); *A61M 16/0677* (2013.01); *A61M 16/202* (2013.01)

(58) Field of Classification Search
USPC .......................... 128/203.12–203.15, 203.22, 128/204.11–204.12, 204.18, 204.21, 128/204.23, 204.26, 205.24, 207.18
See application file for complete search history.

(56) References Cited

U.S. PATENT DOCUMENTS

| | | | | | |
|---|---|---|---|---|---|
| 4,077,404 | A | * | 3/1978 | Elam | 128/204.28 |
| 4,249,527 | A | * | 2/1981 | Ko et al. | 128/204.18 |
| 4,278,110 | A | * | 7/1981 | Price et al. | 137/805 |
| 4,802,362 | A | * | 2/1989 | Haynes | 73/249 |
| 6,615,831 | B1 | * | 9/2003 | Tuitt et al. | 128/204.18 |
| 2002/0092527 | A1 | * | 7/2002 | Wood | 128/207.18 |
| 2002/0157674 | A1 | * | 10/2002 | Shikani et al. | 128/207.29 |
| 2004/0163647 | A1 | * | 8/2004 | Figley et al. | 128/204.18 |
| 2005/0028823 | A1 | * | 2/2005 | Wood | 128/207.18 |
| 2005/0066976 | A1 | * | 3/2005 | Wondka | 128/207.18 |

* cited by examiner

*Primary Examiner* — Rachel Young
(74) *Attorney, Agent, or Firm* — Knobbe Martens Olson & Bear, LLP

(57) ABSTRACT

A breathing gas delivery system and method provides a flow of breathing gas to a patient. The gas flow is purposely interrupted for the patient's exhale phase in order to minimize irritation and injury to nasal tissues due to constant, uninterrupted flows. Embodiments include an oscillating ball valve that interrupts oxygen supply during the patient's exhale phase, cannula tips that are shaped to minimize trauma, and a sleep apnea treatment system that interrupts breathing gas supply during the patient's exhale phase.

15 Claims, 16 Drawing Sheets

BREATHING GAS DELIVERY SYSTEM AND METHOD

RELATED APPLICATIONS

This application claims priority to U.S. Provisional Application Nos. 60/819,751, which was filed on Jul. 10, 2006, and 60/844,125, which was filed on Sep. 11, 2006. The entirety of each of these priority applications is hereby incorporated by reference.

BACKGROUND OF THE INVENTION

Many therapeutic medical treatments include the administration of therapeutic oxygen or other breathing gases to patients. Typically, a nasal cannula is used to deliver such gases. The cannula typically includes a cannula tip that is inserted at least partially into the patient's nose and discharges breathing gases within the patient's nasal passages. When a patient requires prolonged oxygen administration, the cannula is worn during both awake and sleeping hours. During such prolonged use, conventional cannula tips can become a source of irritation for the patient. Prolonged oxygen flow, especially constant flow, through such cannula tips, and even the cannula tips themselves, may cause trauma to the patient's nasal passages. For example, sores, deterioration, and the like may be prompted by constant oxygen flow and/or cannula tips in a patient's nasal passageway. Also, constant oxygen flow wastes oxygen when the patient exhales.

One therapeutic breathing treatment treats sleep apnea, in which a patient tends to stop breathing from time to time while sleeping, thus causing the patient to wake repeatedly during sleeping hours. The patient may not remember awakening during the night, but typically suffers from inefficient and ineffective sleep. A treatment for sleep apnea includes supplying a continuous flow of breathing air to the patient's airway in order to keep the airway open. Although this treatment typically keeps the airway open, and helps the patient to keep breathing, the constant flow of breathing gases can cause irritation to the nasal passageways. Another sleep apnea treatment, referred to as "bi-level" treatment, supplies a continuous flow of air to the patient's airway, but supplies a lesser volume of air during the patient's exhalation phase. Although the flow of air is reduced for some of the time, the flow is still continuous, thus prompting irritation of the nasal passageway by the treatment device. Also, during exhalation, a patient still must overcome the force of air being blown into the airway.

SUMMARY

Accordingly, there is a need for an improved nasal cannula system that regulates the flow of oxygen while the patient is exhaling. Such a system will save oxygen, and will reduce patient discomfort by relieving the nasal passageway from a constant oxygen flow.

In accordance with one embodiment, the present invention provides a gas diverter valve comprising a valve body having an input passage and a common passage. A first path is defined through the valve body from the input passage to the common passage. A second path is defined through the valve body from the common passage to an exhaust port. A chamber is defined within the valve body and enclosing a ball adapted to oscillate between a first position and a second position. When the ball is in the first position the ball obstructs the second path and opens the first path. When the ball is in the second position the ball obstructs the first path and opens the second path.

In one such embodiment, each of the first and second paths extend through the chamber. In another embodiment, the common passage is sized to accommodate a larger gas volume than the input passage. In yet another embodiment, the valve body is formed of a substantially transparent material, and the ball is formed of a colored material so that oscillation of the ball within the valve chamber is observable from outside the valve.

In accordance with another embodiment, the present invention provides a nasal cannula system. The system comprises a valve having a supply connector, a delivery connector, and a valve body defining an internal chamber and a first and second flow path. The first path extends between the supply connector and the delivery connector and passes through the chamber. The second path extends from the delivery connector to an exhaust port and passes through the chamber. A ball is enclosed within the chamber and is adapted to oscillate between a first position and a second position. The ball blocks the second flow path when in the first position and blocks the first flow path when in the second position. An inhalant gas supply is connected to the valve supply connector and is adapted to supply a flow of inhalant gas. A nasal cannula tip communicates with the delivery passage and is adapted to fit in a patient's nose. Inhalant gas is delivered through the valve along the first flow path to the cannula tip and into the patient's nose during a patient inhaling phase. Exhalation gas from the patient flows through the cannula tip and through the valve along the second flow path during a patient exhaling phase.

In one such embodiment, the inhaling gas is continuously supplied at a generally constant pressure that urges the ball toward the second position. In a further embodiment, the valve is adapted so that during the patient exhaling phase exhalation gas urges the ball into the first position so as to interrupt flow of inhalant gas and to open the second flow path.

In accordance with yet another embodiment, a sleep apnea treatment device is provided and comprises an air flow generator adapted to create a positive flow of air at a relatively constant volumetric rate, a supply conduit for delivering the flow of air to a patient, a valve assembly comprising a valve adapted to selectively divert the flow of air from the conduit, and a controller for controlling operation of the valve. The controller comprises a timer timed to a desired positive air flow delivery time and a desired positive air flow interruption time generally corresponding to the patient's desired inhalation period and desired exhalation period. Operation of the valve is controlled depending on the timer so that the positive air flow is delivered to the conduit during the positive air flow delivery time, but is diverted from the supply conduit during the positive air flow interruption time.

In one such embodiment, the valve is adapted so that the positive air flow is substantially totally diverted from the supply conduit during the air flow interruption time. In another such embodiment, the valve is adapted so that the positive air flow is only partially diverted from the conduit during the air flow interruption time.

In yet another embodiment, the device is configured so that, upon a fault of the device, the valve defaults to a position at which full positive air flow is delivered to the supply conduit. In a further embodiment, the valve assembly comprises a solenoid adapted to actuate the valve between a flow diversion position in which positive air flow is diverted away from the supply conduit and a flow communication position in which positive air flow is not diverted from the supply conduit. A yet further embodiment additionally comprises a mechanical biasing member adapted to bias the valve toward the flow communication position, wherein the solenoid is adapted to overcome the bias in order to move the valve to the flow diversion position. In a still further embodiment, the mechanical biasing member comprises a spring.

In accordance with still another embodiment, a nasal cannula tip adapted to extend at least partially into a patient's nasal passage is provided. The nasal cannula tip comprises an elongate body having a proximal end and a distal end. The elongate body encloses a lumen and has an outlet opening at the distal end. The outlet opening has a major axis that is generally greater than a minor axis. The major axis extends in a generally front-to-back direction and the minor axis extends in a direction generally from side-to-side. Air flow through the outlet is spaced from side walls of the nasal passage.

In one such embodiment, the body is rounded at the distal end, and the outlet opening has a generally smaller cross-sectional area than the lumen. In another such embodiment, the body has a front side and a rear side, and the front side is generally tapered toward the distal end so as to generally follow the curvature of a patient's nasal passage.

In yet another such embodiment, the elongate body comprises front and rear ends and opposing sides extending between the front and rear ends, and the body has a generally flattened cross-sectional shape in which the opposing sides are generally closer together than are the front and rear ends. In a still further embodiment, the body comprises a wall having a thickness and an outer surface, and the wall curves about a radius at or adjacent the distal end of the tip. In still another embodiment, the outlet is defined by an outlet edge, and a distance between the outlet edge and the closest side is greater than the thickness of the wall.

In accordance with a still further embodiment, the present invention provides a breathing gas delivery system comprising a first valve and a second valve. Each of the valves have a first port, a second port, and an oscillating member. The first port is adapted to connect to a source of pressurized breathing gas. An inlet passage is defined from the first port to the second port when the oscillating member is in a first position. The inlet passage is closed when the oscillating member is in a second position. Each of the second ports is generally upwardly-opening. The first valve has a first connector, and the second valve has a second connector. The first and second connectors are adapted to adjustably engage one another so as to attach the first and second valves together so that a space is defined between the first and second valve second ports. The first and second connectors are adjustable so that the space between the second ports can be selectively adjusted.

In one such embodiment, the first connector is a male connector and the second connector is a female connector, and the connectors are sized and adapted to engage one another in a friction-type engagement. In another embodiment, the second port has a greater cross-sectional area than the first port.

DETAILED DESCRIPTION OF PREFERRED EMBODIMENTS

FIGS. 1-5 illustrate components and assembly of an embodiment of an oscillating ball diverter valve 30. FIG. 6 illustrates an embodiment of a nasal cannula system 32 that employs a pair of such diverter 30 valves. The nasal cannula system 32 of FIG. 6 employs aspects from Applicants' U.S. Pat. No. 6,763,832, the entirety of which is hereby incorporated by reference. In accordance with the illustrated embodiment, a constant, low pressure flow of oxygen is supplied to the valve 30. As the patient inhales, the oxygen flows through the valve 30 and into the patient's nose. When the patient exhales, the exhaling flow overcomes and stops the flow of oxygen, and exhausts exhalation gases. As such, the constant flow of oxygen directed at the patient's nasal passages is disrupted, thus helping to decrease irritation that such a constant oxygen flow can cause to the patient's nasal passages. Also, the amount of wasted oxygen is decreased. In this specification, the embodiment described in connection with FIGS. 1-5 illustrates one preferred structure for an oscillating ball diverter valve 30 that can be used in such a breathing gas delivery system.

Figure 1A:
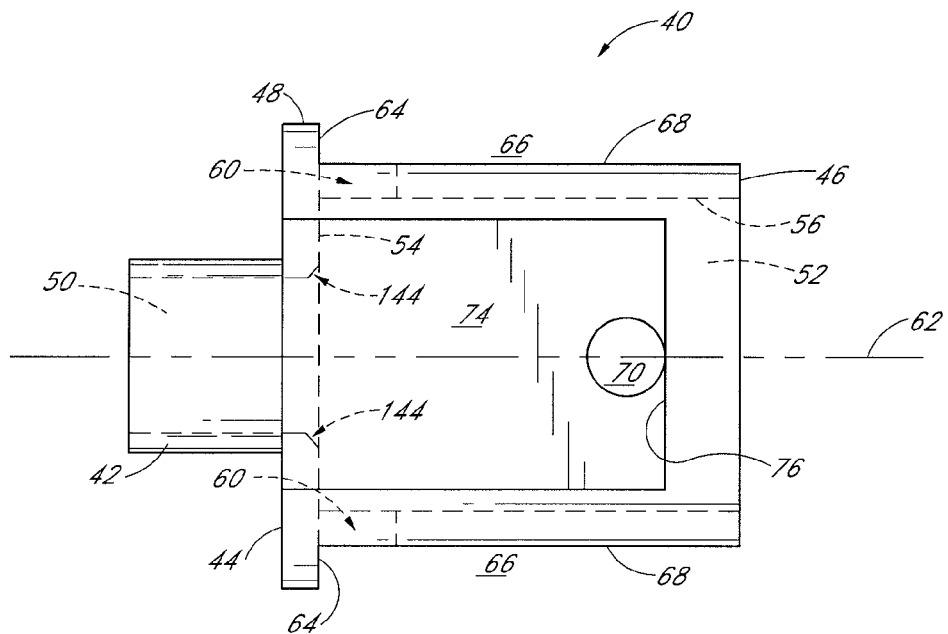
FIG. 1A is a side view of a valve inner body having features in accordance with an embodiment.
Figure 1B:
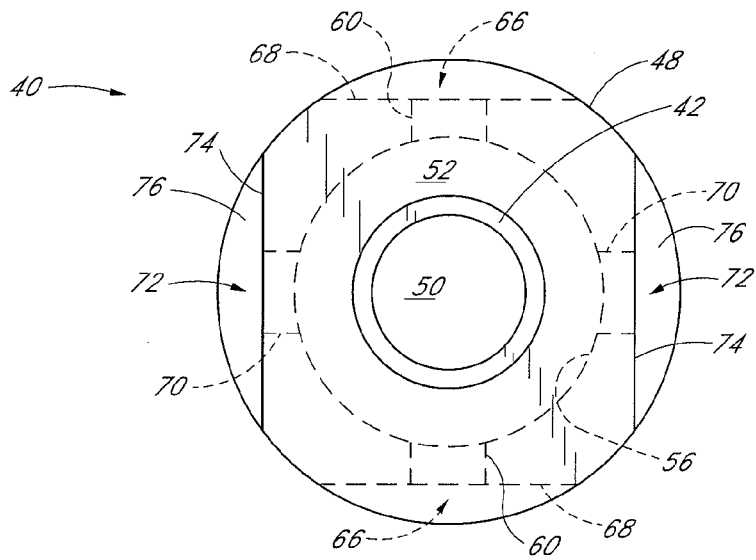
FIG. 1B is an end view of the valve inner body of FIG. 1A.

With reference to FIGS. 1A and 1B, a valve inner body 40 is illustrated. The inner body 40 comprises an upstream connector 42 that is adapted to connect to an oxygen supply tube. The upstream connector 42 leads to a front wall 44 of the inner body 40. A back wall 46 is positioned opposite the front wall 44. An outer peripheral wall 48 extends generally between the front and back walls 44, 46, and is generally circular in profile, as best shown in FIG. 1B. An inhale passage 50 is provided in the upstream connector 42 and leads to a hollow chamber 52 within the inner body 40. In the illustrated embodiment, the hollow chamber 52 is defined by a front wall inner surface 54 and a chamber wall 56 that is disposed circumferentially about the chamber 52. The chamber 52 opens through the back wall 46 of the inner body 40.

A pair of inhale apertures 60 are formed through the chamber wall 56 adjacent the front wall 44 and are directed generally transverse to a longitudinal axis 62 of the inner body 40. An inhale cavity front wall 64 is positioned opposite the inner body front wall 44 and adjacent each inhale aperture 60. Inhale cavities 66 are formed behind the inhale cavity front wall and communicate with the inhale apertures 60. Each inhale cavity 66 has an inhale cavity surface 68 and extends rearwardly to and through the back wall 46.

A pair of opposing exhale apertures 70 are also formed through the chamber wall 56 and generally transverse to the longitudinal axis 62, but are spaced longitudinally from the inhale apertures 60, and are offset therefrom so as not to communicate with the inhale cavities 66. In the illustrated embodiment, each exhale aperture 70 is offset about 90 degrees about the longitudinal axis relative to the adjacent inhale aperture 60. A pair of opposing exhale cavities 72 are defined by an exhale cavity surface 74 and an exhale cavity back wall 76. Each exhale aperture 70 communicates with a corresponding exhale cavity 72, which extends forwardly and through the front wall 44 of the inner body 40.

Figure 2A:
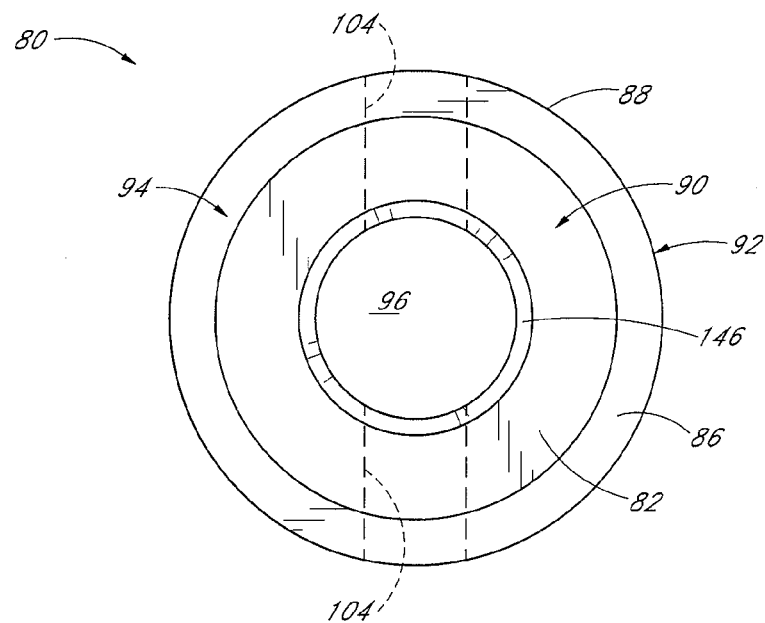
FIG. 2A is an end view of an insert for use in conjunction with the valve inner body of FIGS. 1A-B.
Figure 2B:
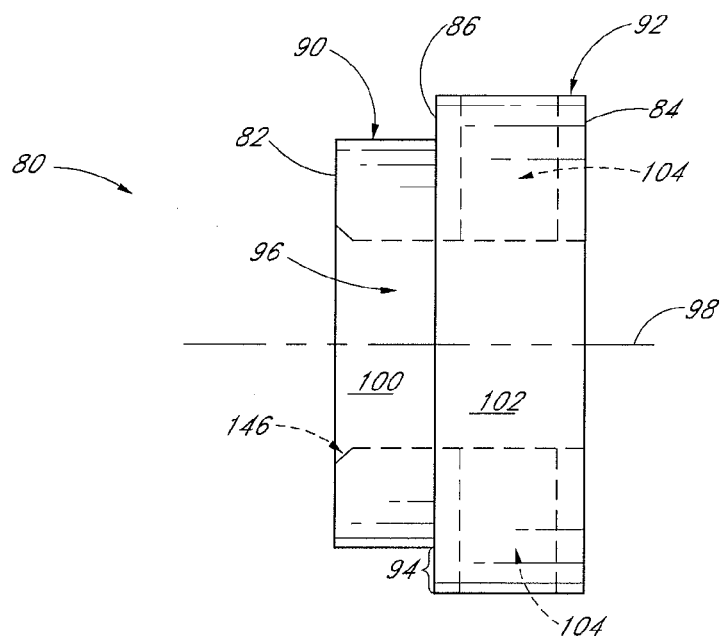
FIG. 2B is a side view of the insert of FIG. 2A.

With reference next to FIGS. 2A and 2B, a valve insert 80 comprises a front wall 82, an opposing back wall 84, and an intermediate wall 86. The insert 80 preferably has an outer peripheral wall 88 that is substantially circular in cross-section. A front portion 90 of the insert 80 is disposed forwardly of the medial wall 86; a back portion 92 of the insert 80 is disposed rearwardly of the medial wall 86. The front portion 90 preferably has a smaller diameter than the back portion 92, resulting in an offset 94 that defines the medial wall 86. Preferably, the diameter of the front portion 90 is about the same as or complementary to the diameter of the inner body chamber 52. As such, the front portion 90 is sized so that its peripheral wall 88 engages the chamber wall 56 of the valve inner body 40. Also, preferably, the offset 94 is generally the same distance as a width of the back wall 46 of the inner body 40 taken at a point where the inhale cavity surface 68 meets the inner body back wall 46. As such, the inhale cavity surface 48 generally aligns with the insert 80 back portion 92 peripheral wall 88 when the insert 80 front portion 90 is engaged in the chamber.

With continued reference to FIGS. 2A and 2B, a longitudinal passage 96 is formed through the insert 80 along a longitudinal axis 98 of the insert 80. The longitudinal passage 96 includes an exhale portion 100 and a common portion 102. A pair of opposing inhale passages 104 are directed generally transverse to the longitudinal axis 98 of the insert 80. The inhale passages 104 open through the insert back portion 92 perimeter wall 88 and communicate with the longitudinal passage common portion.

Figure 3A:
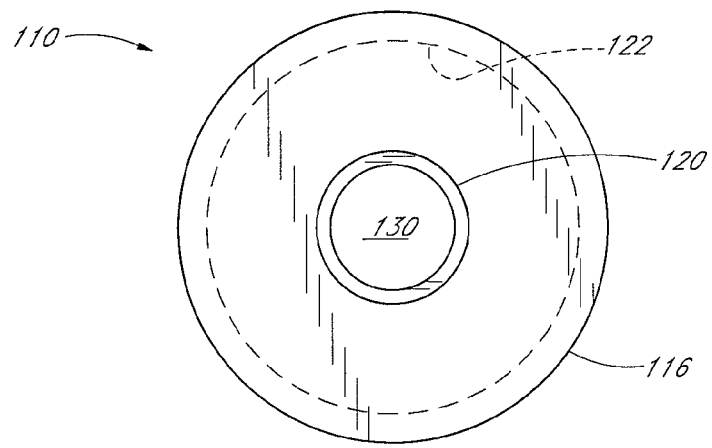
FIG. 3A is an end view of a valve outer body for use in conjunction with the components of FIGS. 1-2.
Figure 3B:
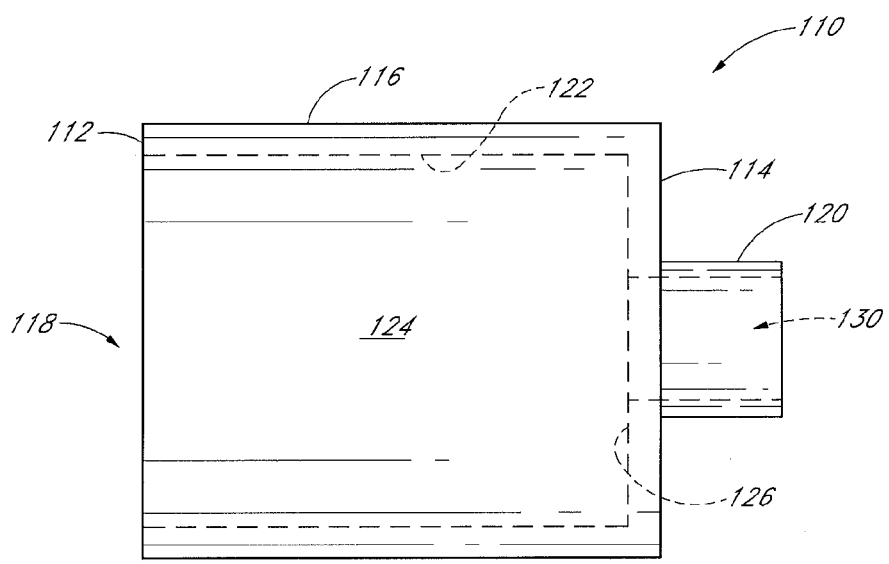
FIG. 3B is a side view of the valve outer body of FIG. 3A.

With reference next to FIGS. 3A and 3B, a valve outer body 110 comprises a front wall 112, an opposing back wall 114, and an outer peripheral wall 116 extending therebetween. The outer peripheral wall 116 is generally circular in cross-section, and the valve outer body 110 is generally cylindrically shaped. A front opening 118 is formed through the front wall 112. A downstream connector 120 extends rearwardly from the back wall 114. An inner peripheral wall 122 is generally circular in cross-section and a space 124 is defined between the inner peripheral wall 122, a back wall inner surface 126, and the front opening 118. A common passage 130 is formed through the downstream connector 1120 and opens into the space 124.

Figure 4:
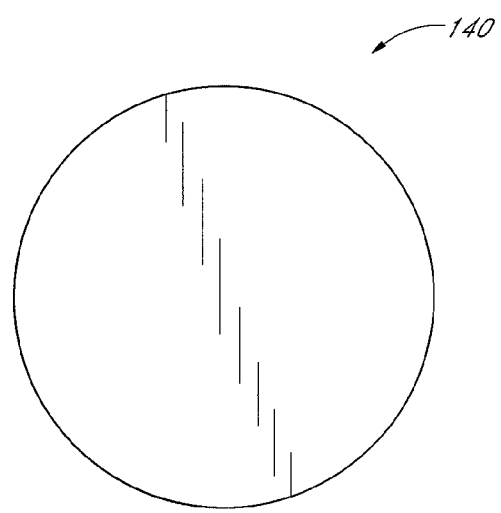
FIG. 4 illustrates a ball adapted to be used in conjunction with the components of FIGS. 1-3.

With reference next to FIGS. 1A, 2B, and 4, a spherical ball 140 is also provided. The ball 140 preferably is sized so as to fit movably within the inner body chamber 52. Preferably, the ball is sized to have a clearance of about 0.001-0.005 inch, and more preferably about 0.001-0.002 inch relative to the chamber wall 56. The valve inner body 40 preferably has a seat 144 formed in the front wall inner surface 54 at the inhale passage 50. The seat 144 is adapted to accommodate the ball 140 to generally close the inhale passage 50 when the ball 140 is engaged with the inner body seat 144. The insert 40 also includes a seat 146 formed in the front wall 82 at the exhale portion 100 of the longitudinal passage 96. The insert seat 146 is adapted to accommodate the ball 140 so as to substantially close the exhale portion 100 when the ball 140 is engaged with the insert seat 146.

Figure 5A:
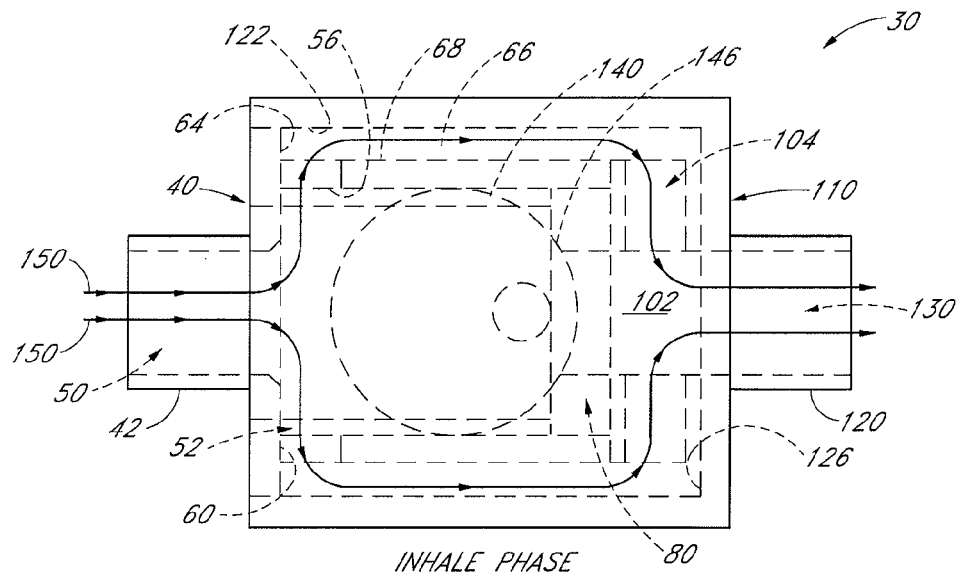
FIG. 5A illustrates an assembled ball diverter valve made using the components illustrated in FIG. 1-4 and showing a flow path of oxygen during a patient inhale phase.
Figure 5B:
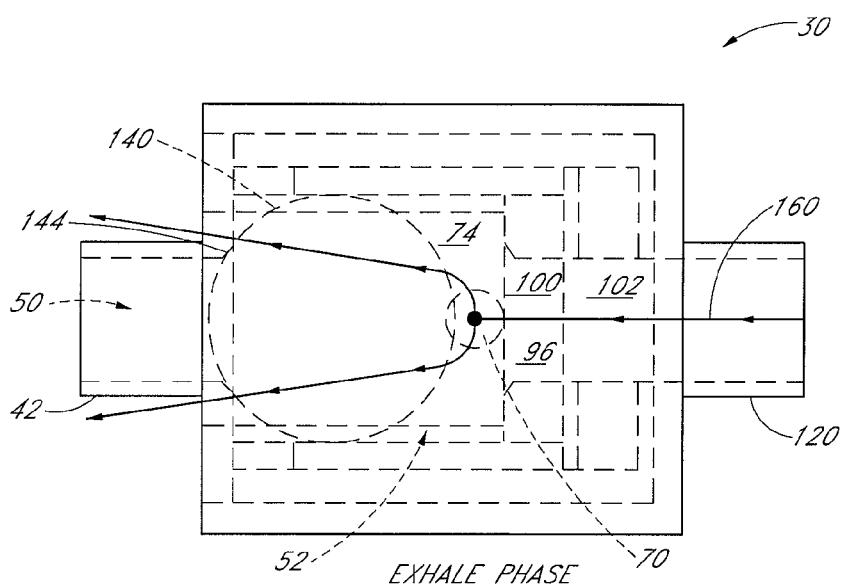
FIG. 5B illustrates the assembled ball diverter valve of FIG. 5A and shows a flow path of oxygen during a patient exhale phase.
Figure 6:
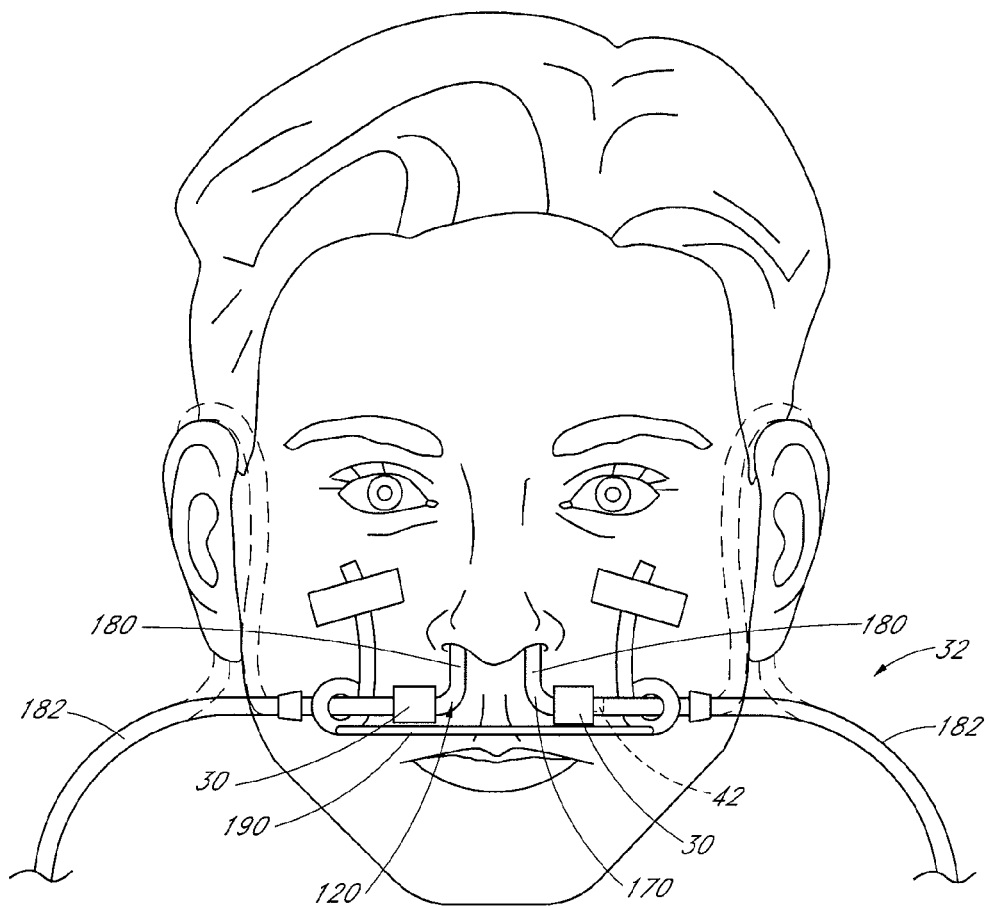
FIG. 6 shows a nasal cannula system employing oscillating ball oxygen diverter valves therein.

FIGS. 5A and 5B illustrate the components described above in connection with FIGS. 1-4 assembled to form a valve 30. FIG. 5A illustrates the assembled valve 30 and shows a flow path 150 therethrough during an inhale phase of the valve. FIG. 5B demonstrates the assembled valve 30 and shows a flow path 160 therethrough during an exhale phase.

As discussed above, the front portion 90 of the insert 80 generally fits into the chamber 52 of the inner body 40 so that the peripheral wall 88 of the insert front portion 90 generally engages the chamber wall 56. The back wall 46 of the inner body 40 generally engages the medial wall 86 of the insert 80. Preferably, the insert 80 is positioned relative to the inner body 40 so that the opposing inhale passages 50 generally align with the inner body inhale cavities 104. Preferably, a portion of the insert back portion 92 peripheral wall 88 generally aligns with the inhale cavity surfaces 68. The ball 140 is arranged within the inner body chamber 52 between the inner body front wall inner surface 54 and the insert front wall 82 and is adapted to oscillate between the inner body seat 144 and the insert seat 146.

The valve inner body 40 and the insert 80 are arranged in the space 124 defined within the outer body 110. Preferably, the diameter of the inner body 40 is such that the outer peripheral wall 48 of the inner body 40 generally complementarily engages the inner peripheral wall 122 of the outer body space 124. The insert 80 is arranged within the outer body space 124 so that the back wall 84 of the insert 80 engages and rests against the back wall inner surface 126 of the outer body 110, and the common passages 102, 130 of the insert 80 and outer body 110 generally align. Preferably, the components are arranged so that when they fit together as shown, the front wall 44 of the inner body 40 generally aligns with the front wall 112 of the outer body 110.

With specific reference to FIG. 5A, an inhale flow path 150 through the valve 30 is illustrated. In an embodiment wherein the upstream connector 42 is connected to a source of oxygen under low pressure, and the downstream connector 120 is connected to a nasal cannula, low pressure oxygen is continuously supplied to the inhale passage 50. When the patient inhales, or when there is no affirmative action by the patient, the oxygen pressure will urge the ball 140 backwardly so that it engages the insert seat 146. With the ball 140 engaged in the insert seat 146, the exhale passage 100 of the insert 80 is blocked from access to the inner body chamber 52. A flow path 150 is defined through the inhale passage 50 and into the chamber 52, then through either of the inhale apertures 60 into an associated inhale cavity 66. Each inhale cavity 66 is enclosed by the outer body peripheral wall 122, and inhale flow continues rearwardly to the insert inhale passages 104, which direct it into the insert common passage 102. The inhale flow path 150 continues through the downstream connector common passage 130 and to the patient.

With specific reference next to FIG. 5B, when the patient exhales, exhalation gases are forced along an exhale pathway 160 through the valve 30. Such exhalation gases flow through the downstream connector common passage 130, into the insert common passage 102, and further to the exhale passage 100. Since patient exhalation is made at greater pressure than inhalation, and at greater pressure than the oxygen supply to the upstream connector 42, pressure from exhalation pushes the ball 140 forwardly so that it engages the inner body seat 144, thus blocking communication with the inhale passage 50 of the upstream connector 42, and accordingly stopping oxygen flow. Moving the ball 140 forwardly also opens access to the exhale apertures 70, which lead to associated exhale cavities 72. The exhale cavities 72 are enclosed by the outer body peripheral wall 122, and thus define an exhale flow path forwardly along the exhale cavity 72, through the inner body front wall 49 and out of the valve 30.

Preferably, the inhale pathway 150 is configured so that the total cross-sectional area along the inhale path is never less than the total cross-section area of the inhale passage 50. For example, the cross-sectional area of the inhale apertures 60, when combined, is at least the same as the cross-sectional area of the inhale passage 50. Preferably, this relationship holds true along the inhale cavities 66 and through the inhale passages 104 of the insert 80, including the common passages 102, 130 of the insert 80 and downstream connector 120. With this structure, flow of inhalant gas is substantially unrestrained through the valve 30.

In the illustrated embodiment, the inhale passage 50 and the common passages 102, 130 are generally the same in diameter and gas flow volume capacity. In another embodiment, the common passage of the downstream connector and the longitudinal passage of the insert have a larger diameter than the inhale passage, and thus can accommodate more gas flowing therethrough. By thus capturing more exhalation gases, this structure better helps the ball overcome the oxygen delivery gas pressure so as to move the ball 140 from the insert seat 146 to the inner body seat 144. In a still further embodiment, the common passage 130 of the downstream connector 120 and the common portion 102 of the insert longitudinal passage 96 are larger than the inhale passage 50 of the upstream connector 42; however, the exhale portion 100 of the insert longitudinal passage 96 has about the same diameter. As such, increased volume of exhalation gases are recruited into the valve body, and such inhalation gas increases in pressure in the exhaust portion 100 to help move the ball 140 to the opposing seat 144 at the start of the exhalation phase.

In a preferred embodiment, the inner body 40, outer body 110, and insert 80 are formed of a substantially transparent polymer, but the ball 140 is formed of a colored material. As such, the ball 140 can be seen within the valve 30, and it can be readily determined how well the oscillating ball diverter valve 30 is working.

Preferably, the valve body 30 is comparatively small. For instance, the ball 140 preferably has a diameter of about ¼ inch. Most preferably, the ball has a diameter of no less than about 5/32 inch. Additionally, as discussed above, preferably the chamber 52 of the valve inner body 40 is constructed such that the ball 140 has a clearance of about 0.001-0.002 inches. As such, the ball 140 does not quite touch the chamber wall 56 when moving, and instead rides on a cushion of air so as to ease valve operation. Further, preferably the ball is constructed of a lightweight material such as a polymer.

In the illustrated embodiment, the downstream connector 120 is generally straight and aligned with the longitudinal axis of the valve outer body 110. In another embodiment, the downstream connector 120 includes a bend 170 (see FIG. 6). In one embodiment the bend 170 is a 90-degree bend. In still another embodiment, the downstream connector 120 comprises a nasal cannula member 180. For example, in the embodiment illustrated in FIG. 6, an oxygen supply tube 182 is connected to the inhale connector 42, and the valve 30 incorporates a nasal cannula tip 180 as its downstream connector. In another embodiment, opposing valves 30 can be slidably attached to a connecting bar 190 so that the valves and associated cannula tips 180 can be adjustably positioned relative one another.

In another embodiment, however, the downstream connector simply has a bend of up to about 90°, and connects to another member, such as a separately-formed nasal cannula tip, which is configured to be inserted into the patient's nose. Preferably, however, the valve is positioned as close as practical to the cannula opening so as to minimize inhalation of previously-exhaled gasses.

The valve 30 embodiment illustrated in FIGS. 1-5 employs a particular structure having a generally cylindrical outer shape. It is to be understood that, in other embodiments, a valve may have a different outer shape such as rectangular, square, hexagonal, etc. Also, the inner passages of the valve may be arranged differently than as shown in the illustrated embodiment. However, such valve may still accomplish principles of the present invention, including diverting gas by using an oscillating ball, such as, for example, diverting gas between two or more flow paths defined in the valve by using an oscillating ball.

In another embodiment, an oscillating ball valve similar to that described above is employed to selectively provide an inhale pathway. However, there is no exhale path extending completely through the valve. Instead, the portion of the patient's exhalation that enters the downstream opening of the valve provides pressure to urge the ball into position to cut off oxygen flow, and most of the air exhaled by the patient is exhaled from the nostrils directly to the environment without passing through the valve.

Figure 7:
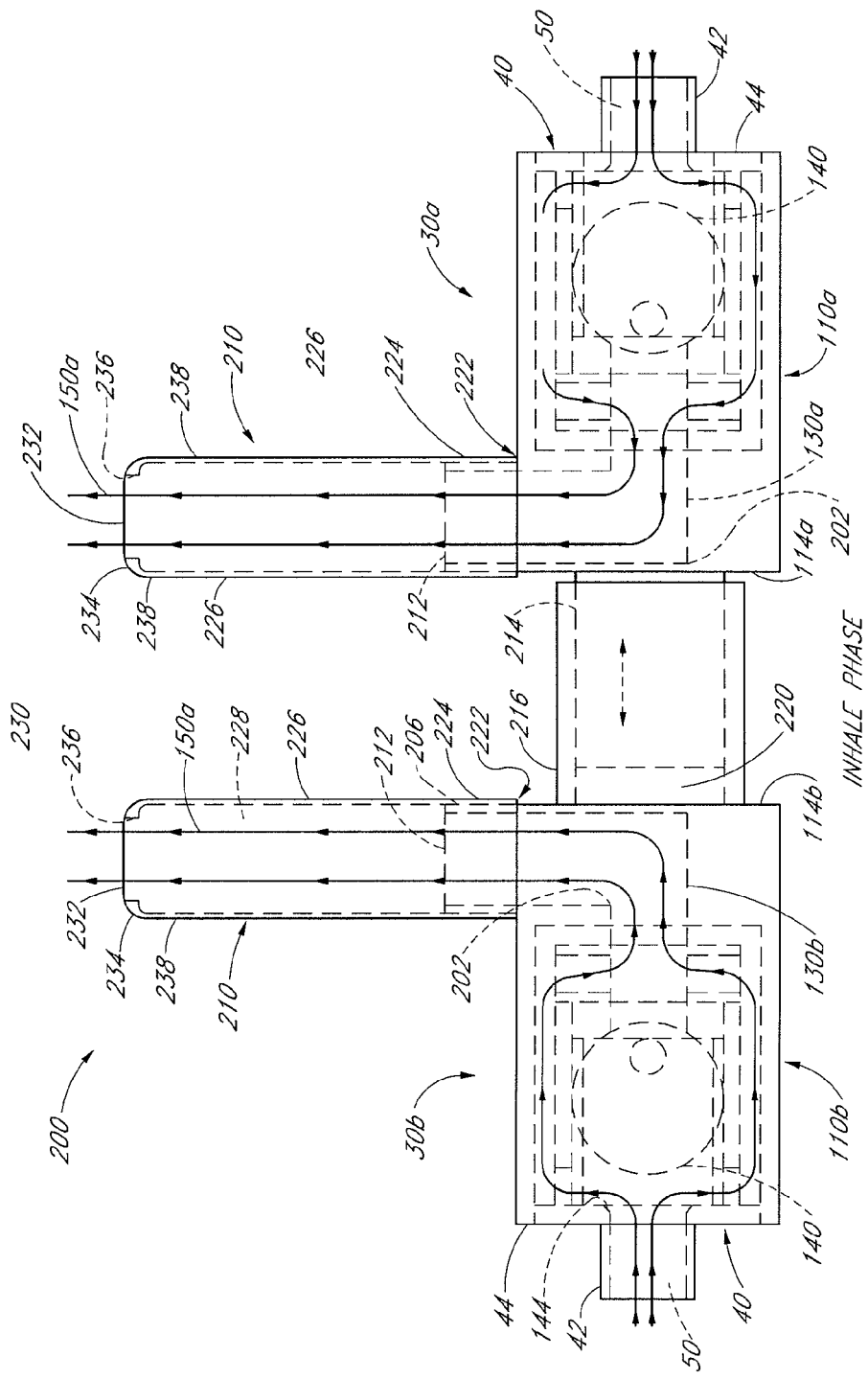
FIG. 7 shows another embodiment of a breathing gas delivery system shown during an inhale phase of a breathing cycle.
Figure 8:
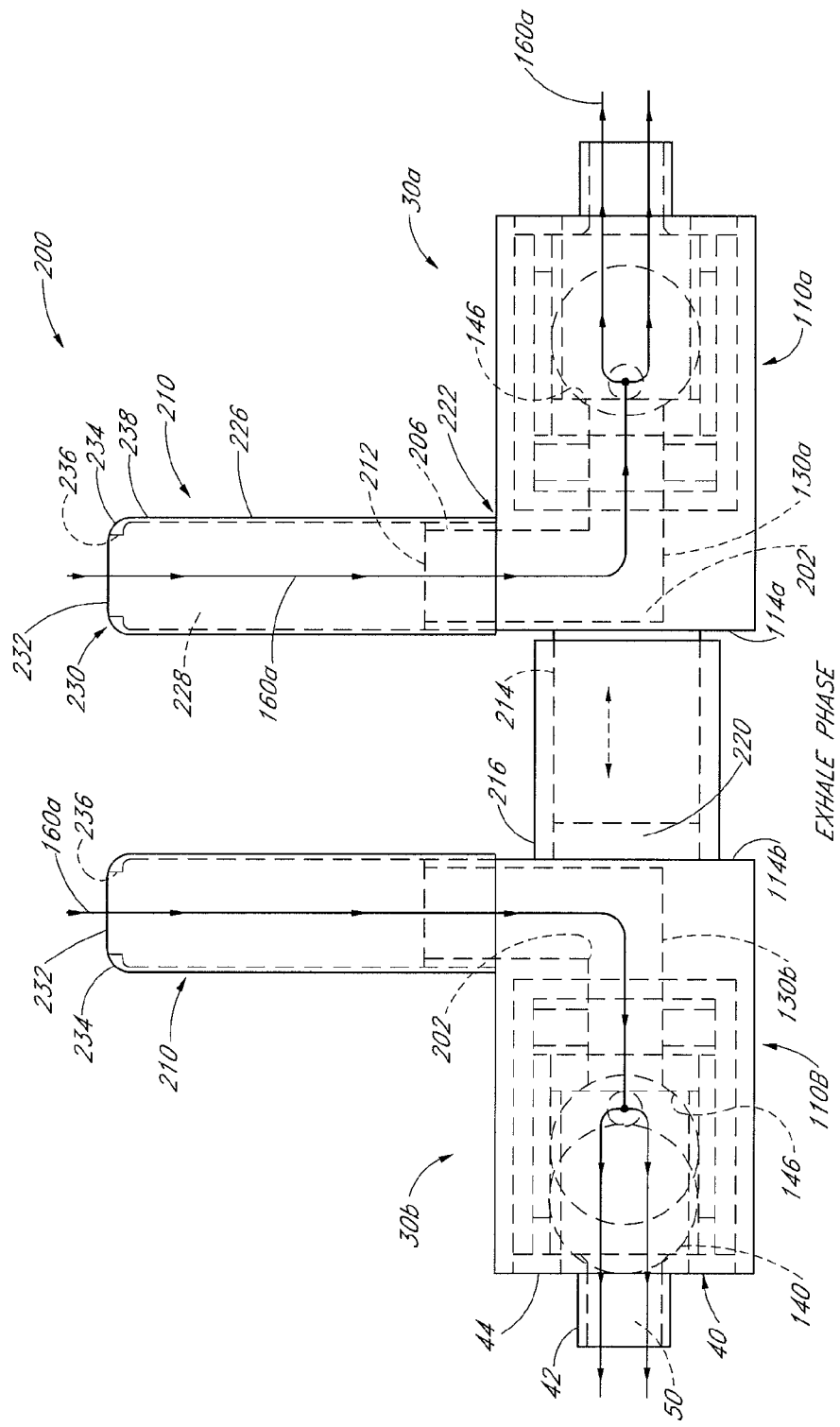
FIG. 8 shows the breathing gas delivery system of FIG. 7 during an exhale phase of a breathing cycle.

With reference next to FIGS. 7 and 8, another embodiment of a breathing gas delivery system is illustrated. In the illustrated embodiment, the system 200 comprises a pair of oscillating ball diverter valves 30a, 30b that are generally similar to the valve 30 discussed above. However, each of the valves 30a, 30b comprises a common passage 130a, 130b that includes a bending portion 202 adapted to change the direction of airflow through the common passage 130a, 130b. In the illustrated embodiment, airflow changes about 90°. The common passage 130a, 130b leads to a cannula connector 206 adapted to be connected to a cannula tip 210, and the common passage 130a, 130b terminates at a common port 212.

In the illustrated embodiment, each of the valves 30a, 30b is constructed similar to the above valve 30 in that the valve inner body 40 is connected to an outer body 110a, 110b, respectively. Preferably, the inner bodies 40 are substantially similar, and have a front wall 44 that supports an upstream connector 42 adapted to connect to an oxygen supply tube. An inhale passage 50 defined in the upstream connector 42 conducts supplied gas into the valve 30a, 30b.

The outer bodies 110a, 110b are adapted to engage respective inner bodies 40. Preferably, the outer bodies 110a, 110b are configured with their common passages 130a, 130b shaped and configured so that the valves 30a, 30b are substantially mirror images of one another as far as their flow paths therethrough go. The common passages 130a, 130b preferably each have a cross-sectional area significantly greater than the cross-sectional area of both of the oxygen supply tubing and the intake passages through the oscillating ball valve. As such, since breathing gases are exhaled at a greater rate than the rate of inhaling, the common passages 130a, 130b can accommodate and take advantage of the increased rate and volume of air so as to overcome the oxygen supply pressure and move the ball 140 to the opposite seat 44 so as to cut off oxygen flow to the patient.

Each of the outer bodies 110a, 110b additionally comprises a back wall 114a, 114b. A male connector 214 extends from back wall 114a and a female connector 216 extends from back wall 114b. In the illustrated embodiment, the male and female connectors 214, 216 are adapted to engage one another so as to adjustably and releasably connect the valves 30a, 30b to one another with their back walls 114a, 114b generally facing each other. Preferably, the male and female connectors 214, 216 are sized and adapted to engage each other with a friction fit that can be releasably adjusted. For example, the depth of the male connector 214 within the female connector 216 can be changed so as to adjust a distance between the back walls 114a, 114b of the respective valves 30a, 30b. As such, the distance between the cannula tips 210 that are connected to the valves 30a, 30b can also be adjusted. This enables customized adjustment for each patient so as to enhance patient comfort and device efficacy. In order to reduce resistance to moving the connectors relative to one another, a small ventilation hole 200 preferably is formed through the female connector 216 near the back wall 114b. The ventilation hole 220 ensures that air pressure within the female connector does not become a significant factor in whether the connectors can be moved relative to one another.

With continued reference to FIGS. 7 and 8, once properly adjusted, the interconnected valves 30a, 30b are in place to selectively provide oxygen to the patient. FIG. 7 shows an inhalation flow path 150a in which oxygen supplied to the valves 30a, 30b urges the ball 140 to seat 146, thus opening access to the flow path 150a. FIG. 8 shows an exhalation flow path 160a in which exhalation gases flow through the cannula tips 210 into valve common passages 130a, 130b to urge the ball to seat 144, thus cutting off pressurized oxygen supply and opening access to the flow path 160a.

With continued reference to FIGS. 7 and 8, preferably the cannula tips 210 are formed separately from the valves 30a, 30b to which they can be selectively attached. A proximal end 222 of the illustrated cannula tip 210 preferably comprises a base portion 224 that is adapted to engage the cannula connector 206 on the respective valve 30a, 30b. Each tip 210 preferably is elongate and is defined by an outer wall 226. A lumen 228 is defined within the outer wall 226. At a distal end 230 of the cannula tip 210, the wall 226 curves somewhat and terminates at a port 232 through which breathing gases may flow. Preferably, the cross-sectional area of the port 232 is no smaller than the cross-sectional area 212 of the common port of the associated valve 30a, 30b and/or no smaller than a cross-sectional area of an associated gas supply tube.

The curved portion 234 of the wall 226 at the distal end 230 provides a blunt surface that is less likely to irritate or traumatize a nasal passage should it come into contact with such a passage. Also, the edges 236 of the port preferably are spaced somewhat from the outer surface 238 of the cannula wall 226. This is in contrast to a conventional cannula tip, which typically has a port formed essentially by simply terminating the outer wall of a straight, elongate tip. In the illustrated embodiment, the curved portion 234 of the wall 226 not only provides a more comfortable surface, but spaces the port 232 from a wall of the patient's nasal passage. As such, supplied breathing gas is directed more towards a center of a nasal passage than with a more conventional cannula tip. This leads to less direct contact of the gas flow against the nasal passage, and thus leads to less irritation and discomfort caused by such flow.

Figure 9:
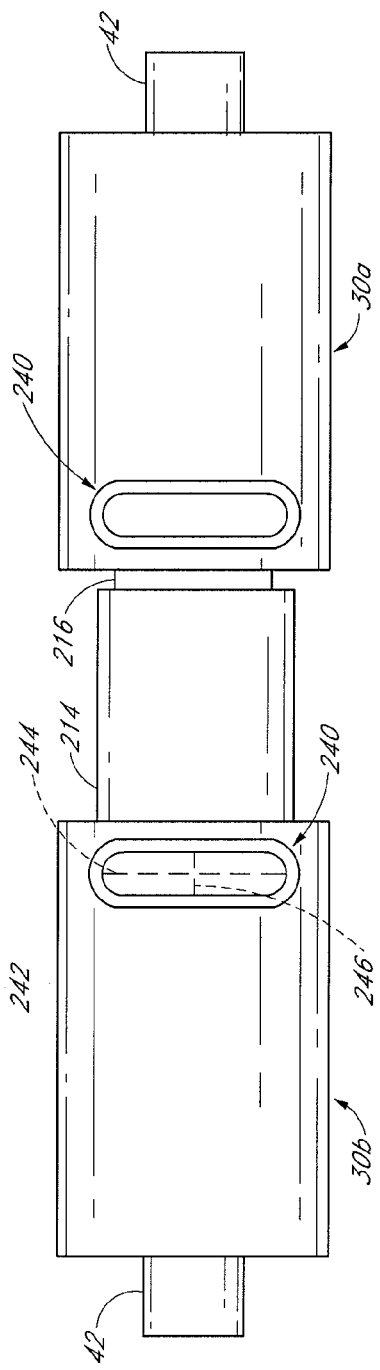
FIG. 9 is a top view of another embodiment similar to the system of FIG. 7.
Figure 10A:
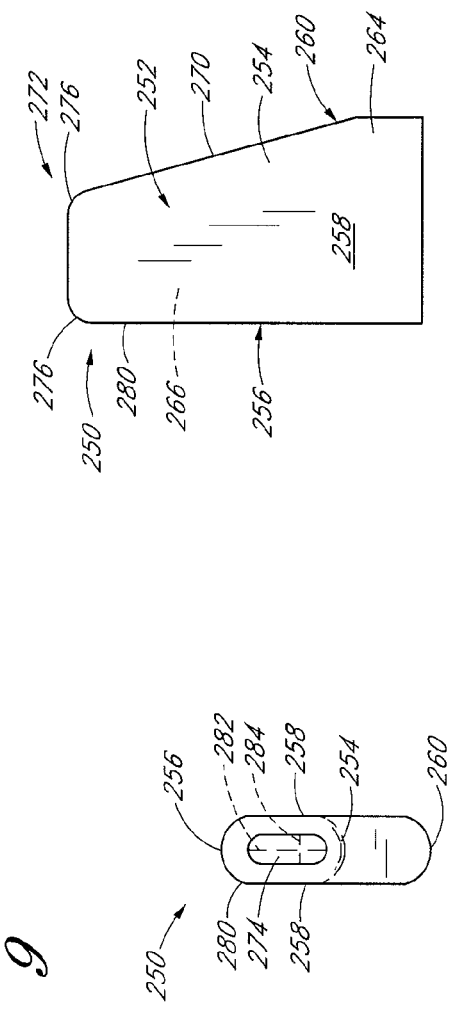
FIG. 10A is a side view of an embodiment of a cannula tip adapted for use with the system of FIG. 9.
Figure 10B:
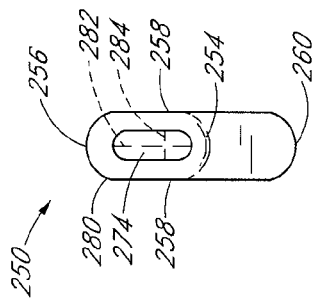
FIG. 10B is a top view of the cannula tip of FIG. 10A.

With reference next to FIG. 9, a top view of the attached valves 30a, 30b is illustrated, but showing an embodiment in which the cannula connectors 240 and common ports 242 are generally oblong in shape. More specifically, each common port 242 has a major axis 244 and a minor axis 246, and the major axis 244 is greater than the minor axis 246. FIGS. 10A and 10B illustrate an embodiment of a cannula tip 250 adapted to engage such oblong ports 242. The illustrated cannula tip 250 comprises an elongate, generally flattened body 252 defining a cannula wall 254. The body 252 has a back portion 256, opposing sides 258, and a front portion 260. A base 264 of the cannula tip 250 is configured to engage an oblong connector 240 such as is illustrated in FIG. 9. A lumen 266 is defined within the body 252 so that breathing gases can flow therethrough. As best shown in FIG. 10A, the front 260 preferably includes a sloping portion 270 that is inclined generally upwardly and rearwardly. The sloping portion 270 is adapted to generally correspond to the sloping shape generally within a patient's nostrils where the cannula tip 250 is employed.

A top 272 of the cannula tip 250 includes a port 274 through which breathing gases may flow. Preferably, a curved portion 276 is provided at the transition from the back 256, front 270, and sides 258 of the tip 250 to the top 272 of the tip 250. Most preferably, this curved edge 276 comprises a portion of the wall 254 that curves about a radius. As in the embodiment discussed above in connection with FIGS. 7 and 8, the port 274 preferably is spaced somewhat from the outer surface 280 of the wall 254. However, the port 274 preferably has the cross-sectional area that is no less than a cross-sectional area of the gas supply line that is attached to the associated valve 30a, 30b.

As shown, the port 274 preferably is generally oblong, having a major axis 282 and a minor axis 284. The major axis 282 preferably runs generally in a direction from the back 256 to the front 270. As such, when breathing gases flow through the port 274, the stream of gas flow generally has an oblong cross-sectional shape as defined by the port 274. This cannula tip 250 configuration directs airflow in a direction and flow shape that is further spaced from the sides of the nasal passage than a more conventional, circular-cross-section cannula tip. Such sides of the nasal passage typically are particularly prone to irritation and trauma when conventional cannula tip structures are used. The cannula tip 250 and port shape 274 of the illustrated embodiment urges the flow of breathing gases in a flow path generally spaced from the sides of the patient's nasal passages, therefore preventing or minimizing airflow against such passages so as to prevent or minimize irritation and trauma.

Preferably, the cannula tips 210, 250 discussed herein are formed of a very flexible material that readily bends upon contact with a surface such as a patient's nasal passages. As such, the walls 226, 254 defining the cannula tip body preferably are very thin. In another embodiment, the cannula tip may have thick walls, and may define a lumen having a cross-sectional area along its length no greater than a cross-sectional area of a gas supply tube.

Figure 12:
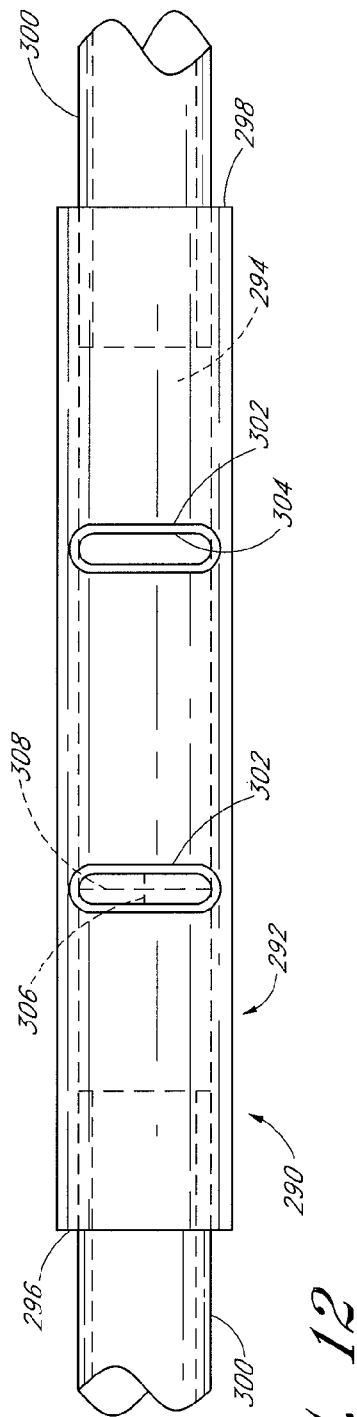
FIG. 12 is a top view of the apparatus of FIG. 11.
Figure 11:
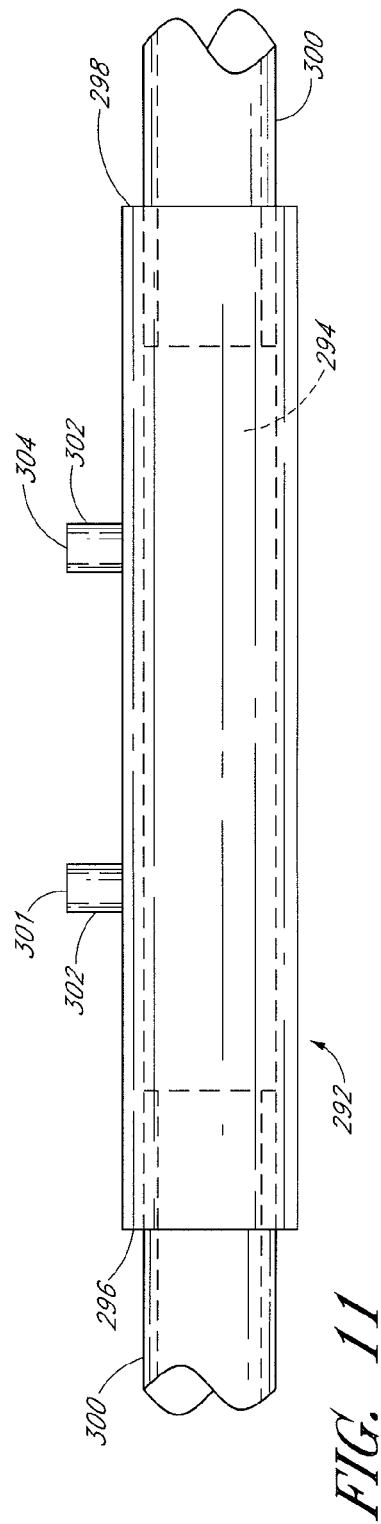
FIG. 11 is a front view of another embodiment of a breathing gas supply apparatus.
Figure 13:
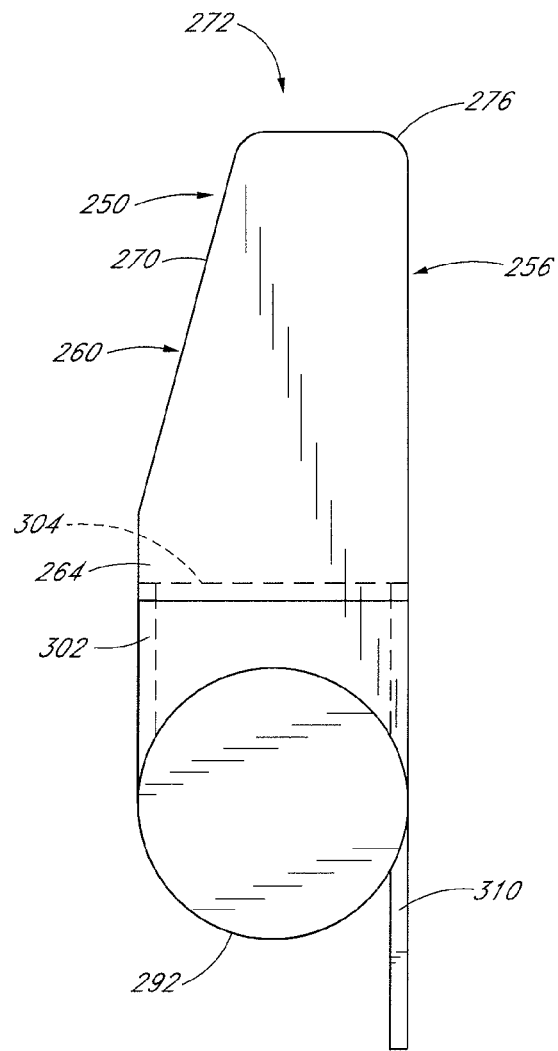
FIG. 13 is an end view of the apparatus of FIG. 11 having a cannula tip attached thereto.

With reference next to FIGS. 11-13, another embodiment of a breathing gas supply apparatus 290 is provided. The illustrated apparatus comprises a connector body 292 that defines a lumen 294 therein and has first and second ends 296, 298 that are adapted to connect to gas delivery tubes 300. In the illustrated embodiment, the delivery tubes 300 fit generally within the ends 296, 298 of the connector body 292. It is to be understood, however, that any type of connection, such as a nipple connector, can be employed.

The connector body 292 preferably comprises two spaced-apart connectors 302, each having ports 304 for delivering breathing gases from the connector body lumen 294 therethrough. Preferably, the connectors 302 are spaced apart in a manner to correspond to a typical patient's nostrils. As with the embodiment just discussed, each connector 302 preferably is generally oblong in shape so that each port 304 has a major axis 306 and a minor axis 308, the major axis 306 being greater than the minor axis 308. Cannula tips 250, such as those described in connection with FIGS. 10A and 10B, can be fit upon the connectors 302. With reference next to FIG. 13, a connector body 292 may comprise a tab 310 for attachment to the face of the wearer. The tab 310 may include an adhesive backing to hold the connector body 292 on the wearer's face or may be adapted to be engageable by adhesive tape.

Nasal cannula tips as discussed above are especially helpful for reducing nasal passage irritation and trauma during long-term therapeutic breathing treatments. Such cannula tips can be used, for example, in connection with certain sleep apnea treatments. In other embodiments, sleep apnea treatment apparatus includes a mask worn by a patient. The mask is configured to receive a flow of air which is directed into the wearer's nose. Preferably, the wearer's mouth is clamped or otherwise kept shut so that air entering the nose flows into the patient's airway as opposed to flowing out of the patient's mouth.

With reference next to FIGS. 14-24, an embodiment of a system and method for treating sleep apnea is provided. In the illustrated embodiment, the system and method involves supplying a positive flow of air to a patient during a patient's inhaling phase, substantially cutting off the positive flow of air to the patient during the patient's exhale phase, and immediately restoring positive airflow to the patient on termination of the exhale phase. As such, air delivery is disrupted so as to reduce irritation to the patient's nasal passages and to prevent interference and resistance to patient exhalation. However, a positive flow of air is provided during the inhale phase in order to keep the patient's airway open and thus prevent the occurrence of apnea. Further, preferably the system and method is configured so that a default position of the system is to have a positive airflow delivered to the patient. Thus, if there is a fault in machine operation or in electricity supply, the system will return to the default of constant positive airflow, thus providing inherently safe operation.

Figure 14:
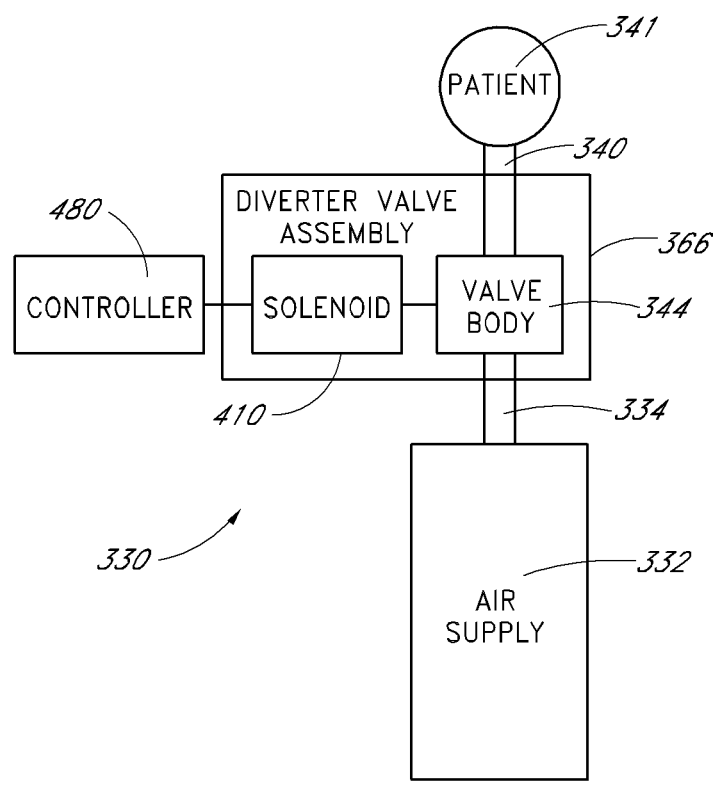
FIG. 14 is a schematic illustration of a sleep apnea treatment system in accordance with one embodiment.

FIG. 14 is a schematic representation of one example embodiment of a system 330 for treating sleep apnea. As shown, the system 330 includes an air supply device 332 configured to generate a positive flow of breathing air into a supply tube 334 at a relatively constant volumetric rate. The supply tube 334 preferably comprises a flexible conduit that leads to a diverter valve assembly 336, which selectively directs the flow of air to an output tube 340 or exhausts the flow to the environment. The output tube 340 preferably comprises a flexible conduit that leads to the patient 341. In one embodiment, a controller 480 controls operation of the valve assembly 336.

Figure 15:
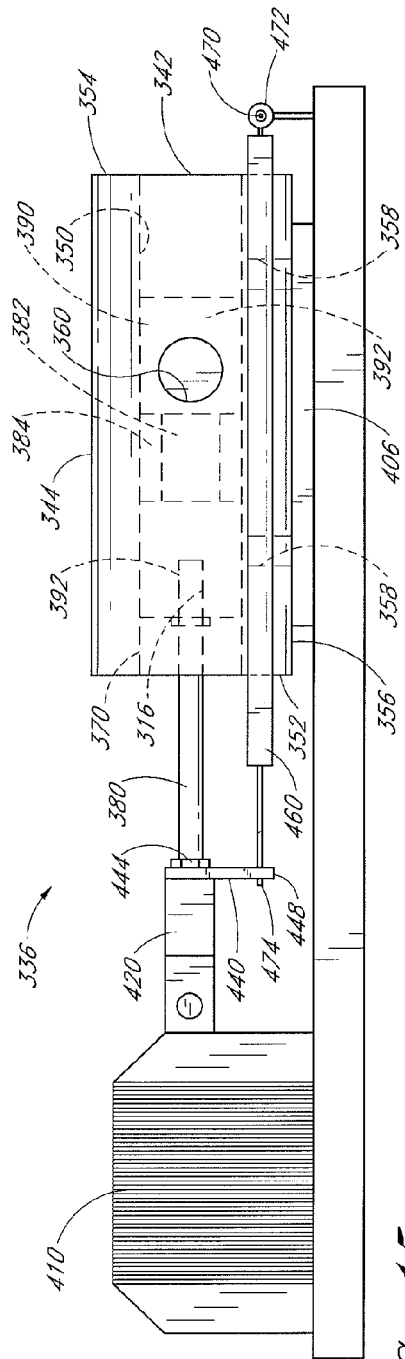
FIG. 15 is a side view of one embodiment of a valve assembly for use in the apnea treatment system of FIG. 14.
Figure 16:
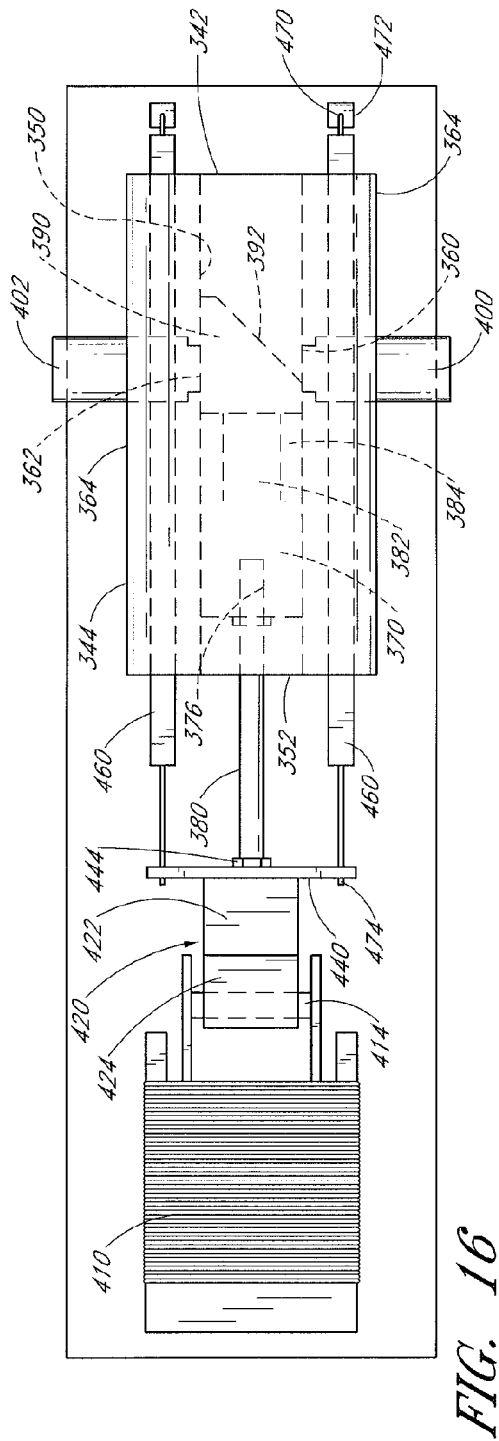
FIG. 16 is a top view of the valve assembly of FIG. 15.
Figure 17:
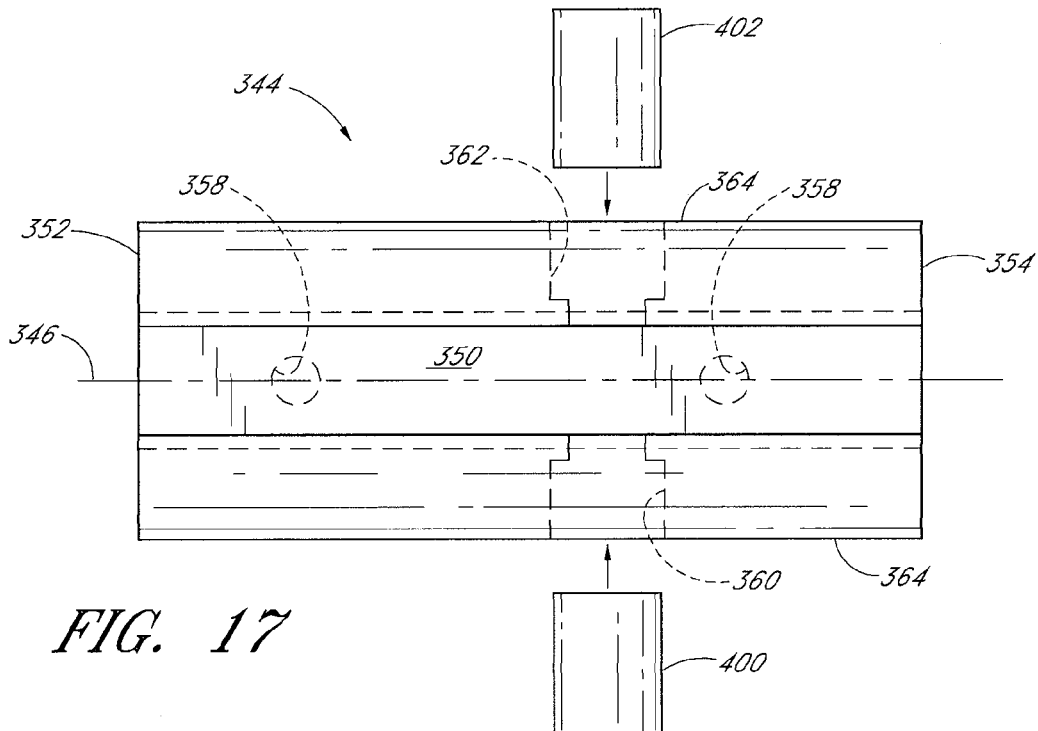
FIG. 17 is a bottom view of a valve body for use in the system of FIG. 15.
Figure 18:
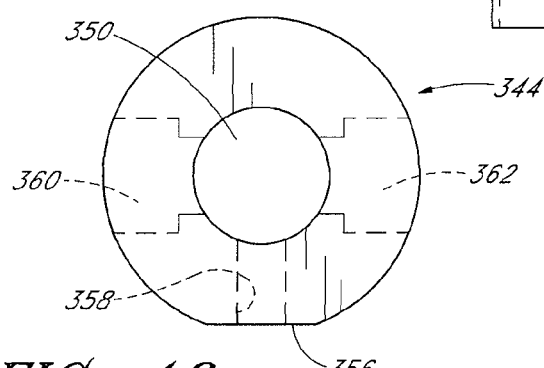
FIG. 18 is an end view of the valve body of FIG. 17.

With additional reference to FIGS. 15 and 16, in operation the diverter valve 336 selectively diverts the flow of air from the output tube 340 to an exhaust port 342, thus periodically supplying and then substantially cutting off positive airflow to the patient. Preferably, the timing of the diverter valve assembly 336 is regulated and chosen based upon breathing patterns of the patient as measured and determined in a test facility such as a sleep apnea treatment facility. In another embodiment, the timing of the diverter valve assembly 336 is determined based upon a desired and/or target breathing pattern developed for the patient by a sleep apnea treatment facility.

With specific reference to FIGS. 15-18, a valve body 344 preferably is elongate along a longitudinal axis 346. A cavity 350 extends longitudinally through the body 344 from a proximal end 352 to a distal end 354. A base surface 356 of the body 344 is substantially flat so that the body 344 can sit on a flat mounting surface, and mount apertures 358 are provided to accommodate screws, bolts, or the like to selectively attach the valve body 344 to the mounting surface. An inlet port 360 and an outlet port 362 extend transversely through opposing walls 364 of the valve body 344 and preferably are substantially aligned with one another.

Figure 19:
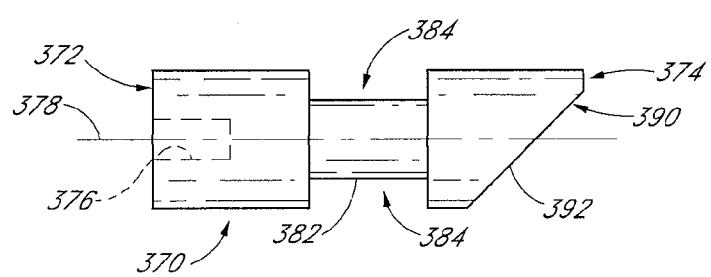
FIG. 19 is a control member for use in the valve body of FIG. 17 in accordance with the system of FIG. 15.

With additional reference to FIG. 19, an elongate control member 370 is sized and adapted fit to slidably fit within the longitudinal cavity 350 of the valve body 344. The control member 370 has a proximal end 372 and a distal end 374. A rod mount cavity 376 at the proximal end 372 preferably extends along a longitudinal axis 378 of the control member 370, and is configured to accommodate an elongate pushrod 380 for controlling movement of the control member 370. A reduced diameter portion 382 of the control member 370 defines a circumferential cavity 384 adjacent thereto. A diverter portion 390 of the control member 370 is provided at the distal end 374. The diverter portion 390 preferably comprises a slanted surface 392. In the illustrated embodiment, the surface 392 is slanted about 45° relative to the longitudinal axis 378.

Figure 20:
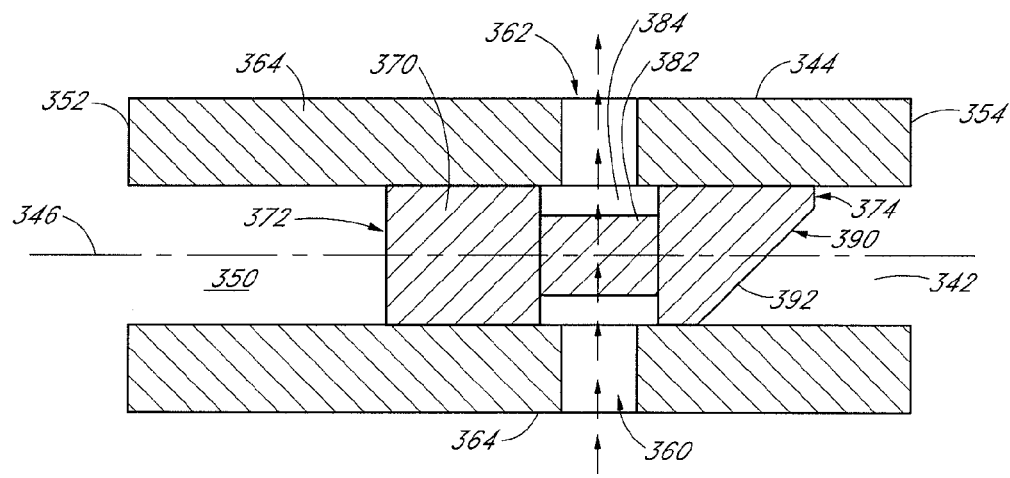
FIG. 20 shows a position of the control member of FIG. 19 within the valve body of FIG. 17 when the system is in an open/supply position.
Figure 21:
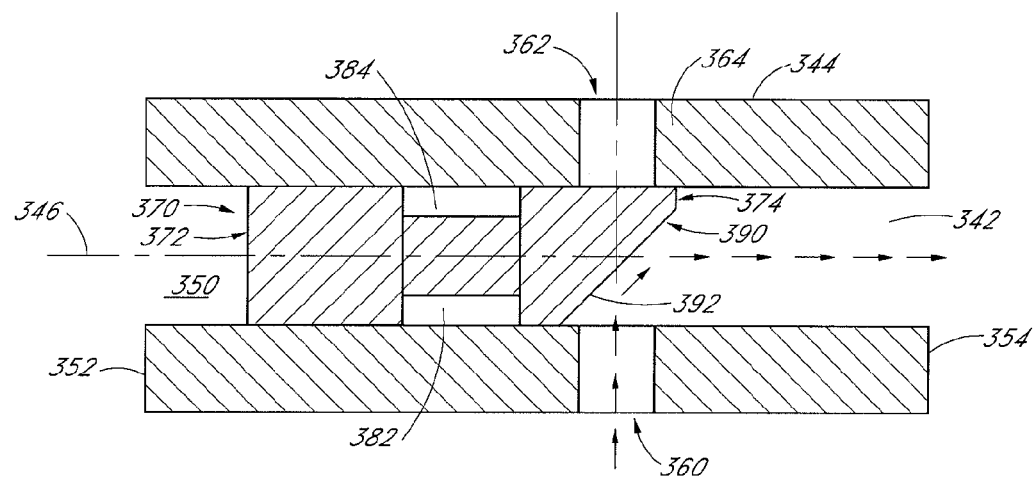
FIG. 21 shows a position of the control member of FIG. 19 within the valve body of FIG. 17 when the system is in a diverted position.

With reference next to FIGS. 20 and 21, operation of the control member 370 within the valve body 344 is schematically illustrated. In a first, supply position as shown in FIG. 20, the control member 370 is disposed within the valve body 344 so that the reduced diameter portion 382 and associated cavity 384 are generally aligned with both the inlet port 360 and the outlet port 362. As such, a positive airflow that is supplied to the inlet port 360 flows through the cavity 384 of the control member 370 and through the outlet port 362.

With reference next to FIG. 21, the control member 370 is depicted in an diverting position in which airflow is diverted to the exhaust port 342. More specifically, in the diverting position the diverter portion 390 of the control member 370 is aligned with the inlet port 360 of the valve body 344. As such, positive airflow through the inlet port 360 is diverted by the diverter portion 390 of the control member 370 into the cavity 350 of the valve body 344. The airflow continues to flow distally through the cavity 350 and out of the cavity 350 through the exhaust port 342 formed at the distal end 374 of the valve body 344.

With reference again to FIGS. 16-17, preferably an inlet connector 400 is attached to the valve body 344 and communicates with the inlet port 360. An output connector 402 preferably is attached to the valve body 344 and communicates with the output port 362. As depicted schematically in FIG. 14, flexible tubing 334, 340 preferably is connected to the inlet and output connectors 400, 402. In the illustrated embodiment, no tubing is connected to the exhaust port 342. However, it is contemplated that in additional embodiments, a tube can be connected to the exhaust port.

With specific reference next to FIGS. 15 and 16, an assembled valve assembly 336 is shown. Preferably, the valve assembly 336 comprises the valve body 344 mounted onto a mount plate 406 so that the base surface 356 of the valve body 344 engages the mount plate 406 and preferably is secured thereto with threaded fasteners that engage the mounting apertures 358 formed in the valve body 344. The control member 370 is disposed in the cavity 350 of the valve body 344 and is arranged to move longitudinally therein with little or no resistance. Preferably, the control member 370 is arranged in the cavity 350 as depicted in FIGS. 20 and 21 so as to selectively direct airflow that is provided to the inlet port 360.

Figure 22:
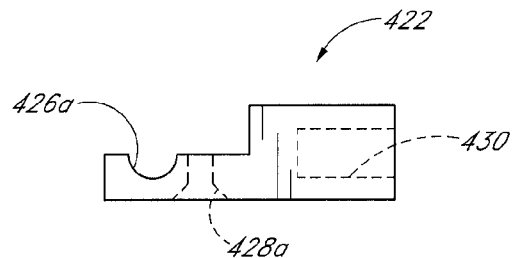
FIG. 22 shows a base portion of a connector for use in accordance with the system of FIG. 15.
Figure 23:
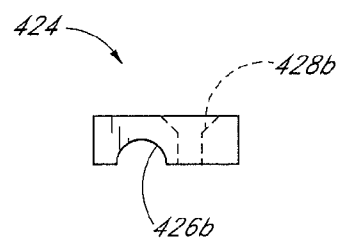
FIG. 23 shows a top portion of a connector for use in accordance with the system of FIG. 15.
Figure 24:
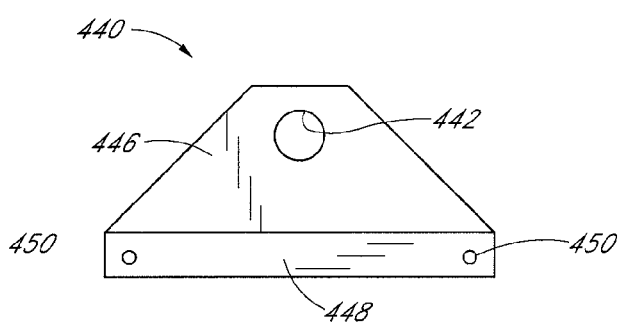
FIG. 24 is a safety member for use in accordance with the system of FIG. 15.

A solenoid 410 is provided to selectively move the control member 370. The solenoid 410 preferably includes a piston that moves longitudinally when the solenoid 410 is actuated. Preferably, the solenoid piston has a connector 414 that facilitates operable connection of the piston to the control member 370. FIGS. 22-24 illustrate members that are assembled to connect the control member 370 to the solenoid connector 414 so that the control member 370 moves longitudinally with the piston and connector 414 when the solenoid 410 is actuated.

With specific reference to FIGS. 22-23, a first connector 420 is adapted to connect to the solenoid connector 414. The first connector 420 comprises a base portion 422 and a top portion 424. Each of the base and top portions 422, 424 comprise a grasp portion 426a, 426b which is adapted to be complementary to at least part of the solenoid connector 414 which, in the illustrated embodiment, is a generally cylindrical rod. In operation, the top portion 424 and base portion 422 are placed about the solenoid connector 414 so as to sandwich and grasp the solenoid connector in between their grasp portions 426a, 426b. Preferably, the base and top portions 422, 424 are fastened together by a fastener such as a bolt arranged through aligned fastener apertures 428a, 428b so that the base and top portions 422, 424 collectively form the first connector 420. A rod mount cavity 430 preferably is provided in the first connector 420 and is adapted to support an elongate rod 380 that also fits into the rod mount cavity 376 formed through the proximal end 372 of the control member 370 (see FIGS. 15-16).

With reference next to FIG. 24, a safety member 440 has a rod aperture 442 adapted to accommodate the push rod 380. As shown in FIGS. 15-16, the safety member 440 preferably is secured to a front end of the first connector 420. Preferably, the push rod 380 is threaded, and a nut 444 holds the safety member 440 in place relative to both the rod 380 and the first connector 420. The safety member 440 comprises a depending portion 446 that depends from the rod aperture 442 and preferably increases in breadth toward a bottom portion 448. Spring connector apertures 450 preferably are provided on opposing sides of the bottom portion 448 of the safety member 440.

With specific reference to FIGS. 15 and 16, preferably a spring 460 or other biasing member has a first end 470 connected to a substantially static spring hold 472, and a second end 474 attached to at least one of the spring connector apertures 450. In the illustrated embodiment, there are two spring connectors 450, facilitating connection to two springs 460, and thus providing redundant safety connection.

In operation, the solenoid 410, when energized, pulls the control member 370 proximally to the diverted flow position as shown in FIGS. 15, 16, and 21. When the solenoid 410 is no longer energized or, in some embodiments, is reversed in polarity, the control member 370 is moved to its default position, which is the full flow supply arrangement illustrated in FIG. 20. If a fault occurs in the solenoid 410 and/or electricity flow, the spring 460 or springs will move and/or secure the control member 370 to the default position, which is a full flow position.

In accordance with a preferred embodiment, a controller 480 (see FIG. 14) is adapted to control the solenoid 410 in accordance with a timer set to actuate the solenoid 410 in accordance with a predetermined breathing cycle time. Most preferably, the patient has undergone therapeutic testing at a sleep therapy clinic or the like so as to determine the appropriate breathing cycle time. For example, a typical adult can be expected to have a sleeping inhale period of about 1½ seconds and an exhale period of about 1 second. The solenoid 410 can be adapted and controlled to operate the valve 336 to have a cycle reflecting such periods or may operate of another cycle time defined for the patient under care of a clinician.

In another embodiment, the solenoid is controlled in accordance with a target breathing pattern determined for the patient by a clinician. Such a pattern is not necessarily based on the patient's existing sleep breathing patterns, but instead by determining an optimal breathing pattern for the patient. In this embodiment, a sudden positive flow of air provided to the patient's airway will prompt the patient to inhale. Such a sudden flow can be provided by the system described herein. As positive airflow supply is substantially cut off, the patient exhales, but is again prompted to inhale when positive airflow is fully restored. As such, the patient's breathing pattern can be controlled or at least modified by the apparatus.

In another embodiment, a similar structure may be employed to provide a bi-level airflow treatment system. For example, the reduced diameter portion of the control member and the associated cavity can be provided very close to the diverter portion, and the solenoid can be set up so that during the exhale cycle a portion of the diverter portion is engaged simultaneously with a portion of the cavity of the control member. As such, positive airflow is still provided to patient during the exhale phase, albeit at reduced volume and rate. Since part of the flow is diverted to the exhaust port, the positive airflow volume provided during the exhale cycle is reduced.

The embodiment illustrated in FIGS. 15-24 shows one structural embodiment that provides a positive airflow that alternates between substantially fully on and fully off according to a prescribed pattern. Further, since the flow of air provided by the air supply is constant, and air flow to the patient is controlled by the valve, there is no delay in flow delivery. For example, there is no requirement to ramp up air pump operation when switching between the fully on and fully off flow conditions. Thus, such switching is substantially instantaneous. It is to be understood that valve assembly configurations other than as shown in the illustrated embodiment can be appropriately employed. For example, another embodiment of a control member may, for example, employ an aperture formed through the control member instead of employing a reduced diameter portion as in the illustrated embodiment. Such a structure will look quite different, yet can have the same operational affect. Additionally, the scale of the valve body and the structure for attaching the solenoid to a control member can be varied as desired to accomplish suitable valve operation and interaction with the solenoid.

In the illustrated prototype the valve assembly is spaced from the airflow supply device. In another embodiment, the diverter valve assembly is incorporated within a housing of the airflow supply device, which comprises a supply hose connection and which also has an exhaust port. In another embodiment, a diverter valve assembly is formed separately from the airflow supply device, but can be attached thereto. Such an embodiment may be especially applicable as a retrofit for an existing airflow supply device for treating sleep apnea. Accordingly, although the illustrated embodiment has been described in detail, it is to be understood that different ways and structural approaches may be used to accomplish its goals and purposes.

Although the present invention explicitly contemplates control of the solenoid by a timer, it is to be understood that other control methods, such as by a controller that weighs inputs obtained by sensors or the like, may be employed. In one embodiment, a sensor detects beginning and/or ending of a patient's exhale phase. Based on such input and other factors, such as anticipated or target exhale phase duration, the valve assembly may be controlled.

During breathing treatments in which a constant flow of breathing gas is supplied to a patient, it is common to add moisture to the breathing gases, especially to breathing gas mixtures having a high content of oxygen, so as to help reduce nasal passage irritation, which can be expected with a constant flow of breathing gas. In additional embodiments that incorporate the sleep apnea system and method in which the positive flow of breathing gas is temporarily completely interrupted, or which incorporate the oscillating ball diverter valve embodiments in which a constant supply of oxygen to the patient is temporarily interrupted, moisture is no longer added to the breathing gas mixture supplied to the patient because the interruption of constant airflow provides significant rest for nasal passage tissues so as to reduce or eliminate irritation and trauma thereto.

Although the inventions herein have been disclosed in the context of certain preferred embodiments and examples, it will be understood by those skilled in the art that the present inventions extend beyond the specifically disclosed embodiments to other alternative embodiments and/or uses of the inventions and obvious modifications and equivalents thereof. In addition, while a number of variations of the inventions have been shown and described in detail, other modifications, which are within the scope of this inventions, will be readily apparent to those of skill in the art based upon this disclosure. It is also contemplated that various combinations or subcombinations of the specific features and aspects of the embodiments may be made and still fall within the scope of the invention. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above, but should be determined only by a fair reading of the claims that follow.

What is claimed is:

1. A breathing gas delivery system, comprising:
   a first valve and a second valve, each of the valves having a first port, a second port, and an oscillating member, the first port of each valve adapted to connect to a tube communicating pressurized breathing gas from a source of pressurized breathing gas, an inlet passage defined from the first port to the second port when the oscillating member is in a first position, the inlet passage being closed when the oscillating member is in a second position, each of the second ports being generally upwardly-opening, each of the first ports being generally horizontally-opening, a nasal cannula tip disposed on each second port, the nasal cannula tips being configured to fit into a patient's nostril, the first and second valves sized and configured to fit between a patient's mouth and nose;
   the first valve having a first connector, and the second valve having a second connector, the first and second connectors adapted to adjustably engage one another so as to attach the first and second valves together so that a space is defined between the first and second valve second ports and so that the first and second valve first ports open in opposite directions;
   wherein the first and second connectors are adjustable so that the space between the second ports can be selectively adjusted, wherein each valve comprises an elongate chamber having an inlet passage seat at one end and an exhale passage seat at the other end, the oscillating member comprising a ball within the elongate chamber, wherein when the oscillating member is in the first position the ball engages the exhale passage seat, and wherein when the oscillating member is in the second position the ball engages the inlet passage seat.

2. A breathing gas delivery system as in claim 1, wherein each valve has an elongate inhale passage adjacent the elongate chamber, and the inlet passage extends from the first port through the inlet passage seat and into the chamber, then to the inhale passage and further to the second port.

3. A breathing gas delivery system as in claim 2, wherein an exhale passage is defined from the second port through the exhale passage seat into the chamber and further to an exhale port.

4. A breathing gas delivery system as in claim 1, wherein the first connector is a male connector and the second connector is a female connector, and the connectors are sized and adapted to engage one another in a friction-type engagement.

5. A breathing gas delivery system as in claim 1, wherein the second port has a greater cross-sectional area than the first port.

6. A gas diverter valve, comprising:
   a valve body having an input passage having an input passage valve seat and a common passage having a common passage valve seat, a first path defined through the valve body from the input passage to the common passage, a second path defined through the valve body from the common passage to an exhaust port, a chamber defined within the valve body and enclosing a ball adapted to oscillate between a first position in which the ball is engaged with the common passage valve seat and a second position in which the ball is disengaged from the common passage valve seat and is engaged with the input passage valve seat, the first path extending through the input passage valve seat and the chamber between the input passage and the common passage, the second path extending through the common passage valve seat and the chamber between the common passage and the exhaust port;
   wherein when the ball is in the first position, the ball obstructs the second path and opens the first path, and when the ball is in the second position the ball obstructs the first path and opens the second path, wherein the valve body comprises an inner body and an outer body, the inner body having an inner body outer wall defining the chamber, a first inhale port being formed through the inner body outer wall, the outer body having an outer body outer wall, the inner body positioned at least partially within the outer body so that the inner body outer wall and outer body outer wall are juxtaposed adjacent one another, the inner body outer wall having an elongate cavity having elongate edges on opposing sides of the cavity, the inner body outer wall configured so that the elongate edges engage the outer body outer wall and an elongate inhale passage is defined between the edges and the inner body and outer body outer walls, the first inhale port communicating the elongate inhale passage with the chamber, the first path extending from the chamber through the first inhale port and to the elongate inhale passage.

7. A gas diverter valve as in claim 6, wherein a second inhale port communicates the elongate inhale passage with the common passage, and the first path extends from the elongate inhale passage through the second inhale port to the common passage.

8. A gas diverter valve as in claim 7, wherein the common passage has a cross-sectional area, and the second inhale port opens into the common passage at a junction, and wherein a portion of the second path between the common passage valve seat and the junction has a cross-sectional area less than the common passage cross-sectional area.

9. A gas diverter valve as in claim 8, wherein the second path extends from the common passage through the portion of the second path between the common passage valve seat and the junction, through the common passage valve seat and into the chamber.

10. A gas diverter valve as in claim 7, wherein the chamber is elongate along a longitudinal axis, the first path is parallel to the longitudinal axis in the elongate inhale passage, and the first path is transverse to the longitudinal axis through the first and second inhale ports.

11. A gas diverter valve as in claim 6, wherein the input passage has an input passage cross-sectional area, and at no point along the first path is a total cross-sectional area of the first path less than the input passage cross-sectional area.

12. A gas diverter valve as in claim 11, wherein the common passage has a common passage cross-sectional area that is greater than the input passage cross-sectional area.

13. A gas diverter valve as in claim 6, wherein each of the first and second paths extend through the chamber.

14. A gas diverter valve as in claim 6, wherein the common passage is sized to accommodate a larger gas volume than the input passage.

15. A gas diverter valve as in claim 6, wherein the valve body is formed of a substantially transparent material, and the ball is formed of a colored material so that oscillation of the ball within the valve chamber is observable from outside the valve.

\* \* \* \* \*